(12) United States Patent
Keating et al.

(10) Patent No.: US 11,547,400 B2
(45) Date of Patent: Jan. 10, 2023

(54) SUTURE DELIVERY SYSTEM

(71) Applicant: SHARP FLUIDICS, LLC, Hayward, CA (US)

(72) Inventors: Ronan Keating, Dublin (IE); Diarmuid Conroy, Dublin (IE); Gerard Rabbitte, Dublin (IE); Claire Picard, Dublin (IE)

( * ) Notice: Subject to any disclaimer, the term of this patent is extended or adjusted under 35 U.S.C. 154(b) by 346 days.

(21) Appl. No.: 16/091,936

(22) PCT Filed: Apr. 19, 2017

(86) PCT No.: PCT/EP2017/059233
§ 371 (c)(1),
(2) Date: Oct. 5, 2018

(87) PCT Pub. No.: WO2017/182492
PCT Pub. Date: Oct. 26, 2017

(65) Prior Publication Data
US 2019/0090869 A1    Mar. 28, 2019

Related U.S. Application Data

(60) Provisional application No. 62/324,422, filed on Apr. 19, 2016.

(51) Int. Cl.
| | |
|---|---|
| *A61B 17/04* | (2006.01) |
| *A61B 17/34* | (2006.01) |
| *A61F 2/00* | (2006.01) |
| *A61B 90/00* | (2016.01) |
| *A61B 17/00* | (2006.01) |

(52) U.S. Cl.
CPC ...... *A61B 17/0482* (2013.01); *A61B 17/0401* (2013.01); *A61B 17/0469* (2013.01); *A61B 17/0493* (2013.01); *A61B 17/3494* (2013.01); *A61F 2/0063* (2013.01); *A61B 2017/00004* (2013.01); *A61B 2017/0053* (2013.01); *A61B 2017/00876* (2013.01); *A61B 2017/0409* (2013.01); *A61B 2017/0417* (2013.01); *A61B 2017/0464* (2013.01); *A61B 2090/08021* (2016.02); *A61F 2002/0072* (2013.01); *A61F 2220/0008* (2013.01)

(58) Field of Classification Search
CPC ............ A61B 17/0483; A61B 17/0469; A61B 17/0493
See application file for complete search history.

(56) References Cited

U.S. PATENT DOCUMENTS

| | | | |
|---|---|---|---|
| 2006/0030868 A1* | 2/2006 | Bennett, III | A61B 17/0482 606/148 |
| 2015/0018850 A1* | 1/2015 | Bagaoisan | A61B 17/0482 606/144 |
| 2015/0038991 A1 | 2/2015 | Prior | |
| 2015/0157316 A1* | 6/2015 | Labarbera | A61B 17/0469 606/144 |
| 2015/0335320 A1* | 11/2015 | Keating | A61B 17/0469 606/144 |

OTHER PUBLICATIONS

International Search Report and Written Opinion for PCT/EP2017/059233 dated Jul. 20, 2017; 11 pages.

* cited by examiner

*Primary Examiner* — Sarah A Simpson
(74) *Attorney, Agent, or Firm* — FisherBroyles LLP; John Shimmick (57) ABSTRACT

A device is described. The device includes a suture guide and a tissue retracting surface to enable accurate and safe delivery of sutures through tissue.

20 Claims, 11 Drawing Sheets

SUTURE DELIVERY SYSTEM

CROSS-REFERENCE TO RELATED APPLICATION

The present application is a national phase entry under 35 U.S.C. § 371 of International Application No. PCT/EP2017/059233, filed Apr. 19, 2017, entitled "SUTURE DELIVERY SYSTEM," which designates the United States of America, which claims priority to U.S. Provisional Application No. 62/324,422, filed Apr. 19, 2016, the entire disclosures of each of these applications are hereby incorporated by reference in their entireties and for all purposes.

FIELD OF THE INVENTION

The present invention relates to a suture delivery system. In one configuration it relates to a suture delivery system which operably provides for deployment of an anchoring or suture deployment system may be usefully employed in surgery.

BACKGROUND

There are difficulties sometimes associated with the closure of wound sites for example, where the defect is greater than two centimetres in length. There are difficulties in particular in finding the fascia layer through which a suture must be passed to ensure good and adequate fascial recruitment and there is also the risk of damaging internal structures when deploying a suture passer. When suturing abdominal wounds a retractor is often used to open the defect and present the abdominal layers to the user making it easier to place the suture through the relevant layers. The device disclosed here provides for retractor functionality while enabling accurate and protected suture deployment.

The consequences of inadequate closure may be serious. For example, the patient may be subject to an early or late onset hernia, wound dehiscence, bowel stricture, infection, or bleeding from the defect.

SUMMARY

These needs and others are addressed in accordance with the present teaching which provides a suture delivery system intended to enable safer and more repeatable wound closure subsequent to a laparoscopic, single port or general surgical procedures where abdominal closure is required. The principle disclosed herein may be applied to a wide variety of closure scenarios.

Accordingly there is provided a device, kit and method as defined in the claims that follow.

These and other features of the present teaching will be better understood with reference to the drawings which follow which are provided to assist in an understanding of the present teaching and are not to be construed as limiting in any fashion.

BRIEF DESCRIPTION OF THE DRAWINGS

The present teaching will now be described with reference to the accompanying drawings in which.

DETAILED DESCRIPTION OF THE DRAWINGS

The teaching of the present invention will now be described with reference to exemplary embodiments thereof which are provided to assist with an understanding of the present teaching and are not to be construed as limiting in any way. It will be appreciated that modifications can be made to the exemplary arrangements which follow without departing from the spirit or scope which is only to be limited insofar as is deemed necessary in the light of the appended claims.

Within the context of the present teaching a suture delivery system advantageously allows for the delivery of suture within an abdominal cavity of the patient. It will be appreciated that the following discussion regarding the specifics of the abdominal cavity and abdominal wall should not be construed as limiting in that a system provided in accordance with the present teaching may be used with other types of tissue including but not limited to organs, bones or the like. The use of a suture delivery system per the present teaching may be used for closure of a wound post completion of a surgical procedure. In such a configuration the device is used to accurately guide the suture or suture anchor assembly, where the suture is coupled to an anchor, through the abdominal wall and is held within the wall by the anchors that will remain deployed within the abdominal cavity, a subsequent tightening of the sutures will cause the sides of the incision, or break in the abdominal cavity to be brought together to close the wound. The adoption of such a technique will advantageously require the use of bioabsorbable anchors, as the anchors will remain within the abdominal cavity during the healing process prior to their ultimate disintegration. For scenarios where permanent support is required, non absorbable sutures and anchros may be used ustiliing materials such as PEEK, PE, Nylon, Stainless Steel, or Nickel Titanium alloys.

In a further embodiment the anchors may be made from a ferromagnetic material so that a magnet could be passed down a trocar and the anchors would be attracted to and adhere to the magnet, allowing them to be drawn out through the trocar. The advantage of this approach is that direct visualisation may not be necessary. Alternatively, the anchors may be themselves magnets and a ferromagnetic pick up device could be employed through the trocar to pick up the anchors.

Figure 1A:
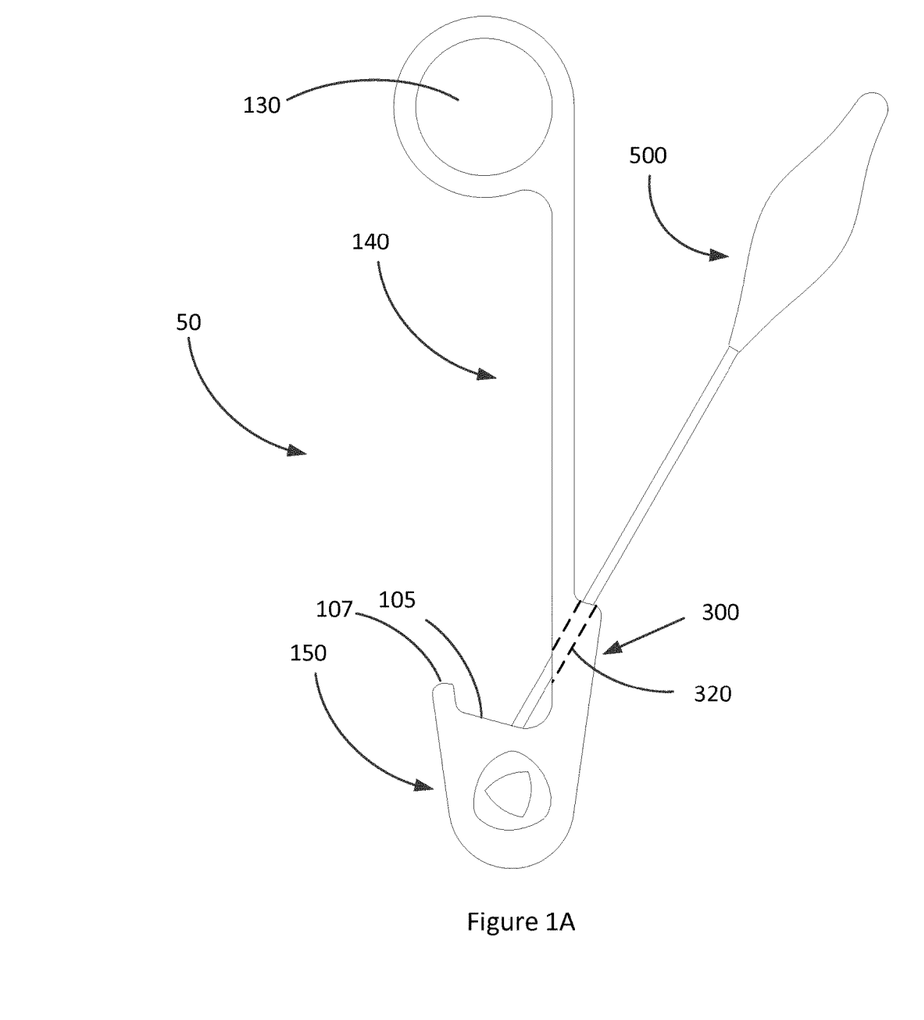
FIGS. 1 and 2 show configurations of devices that may be provided in accordance with the present teaching.
Figure 2:
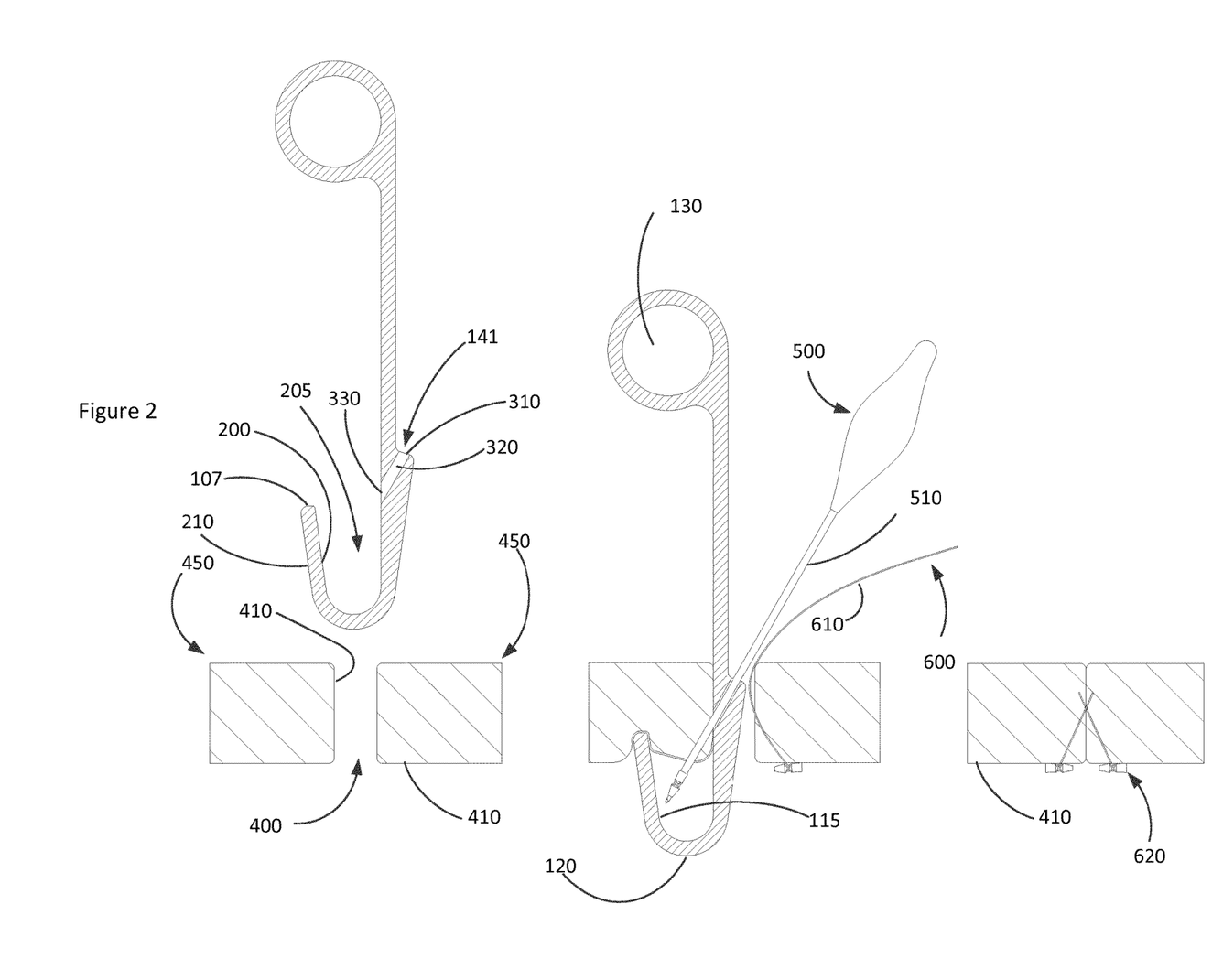
Figure 3A:
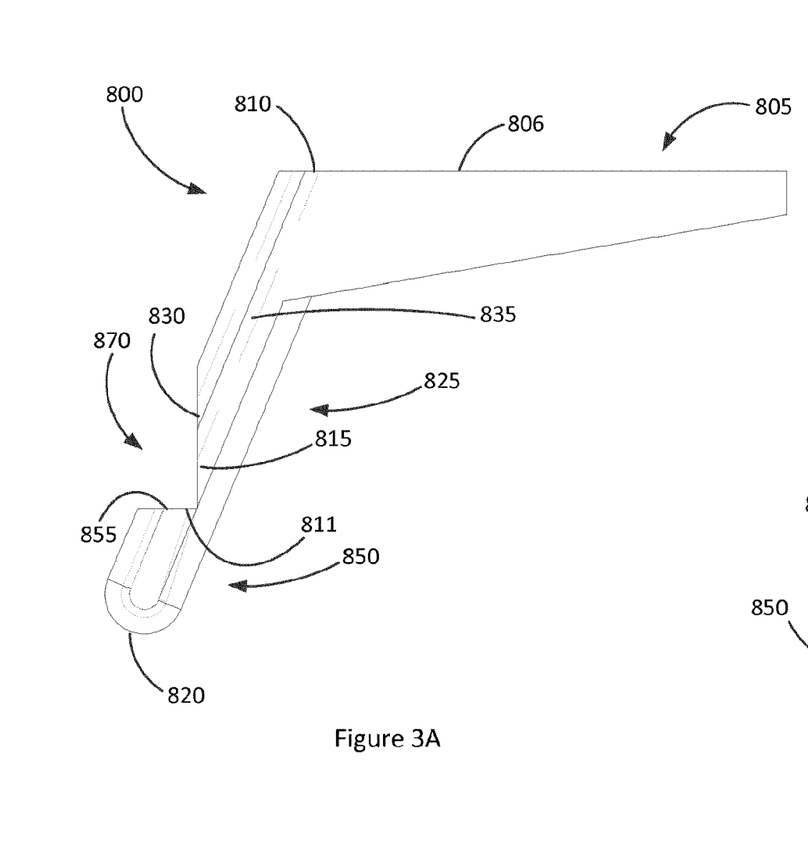
FIG. 3 shows an alternative arrangement of the device of FIG. 1.
Figure 3B:
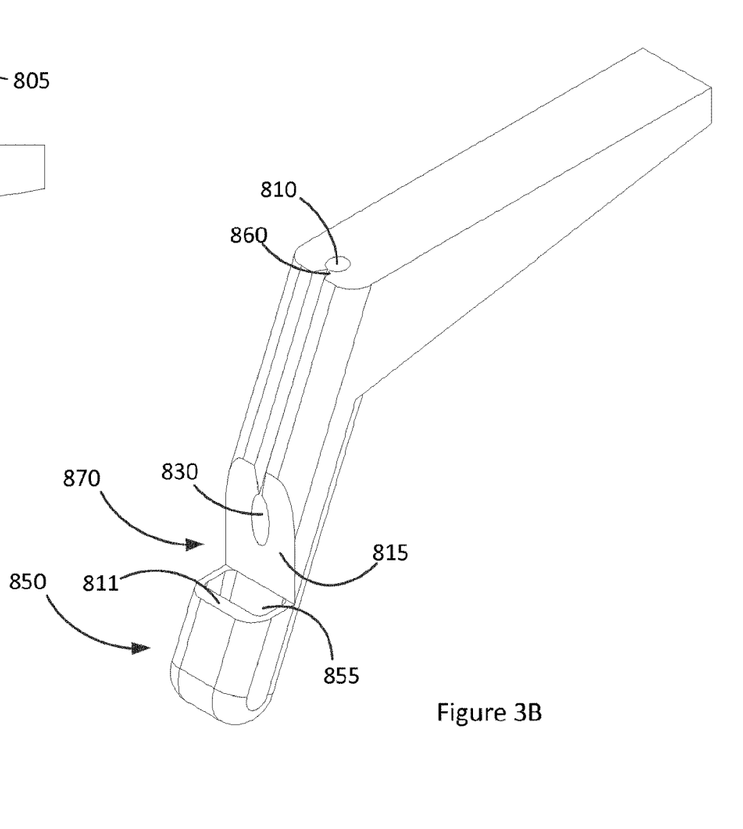
Figure 3C:
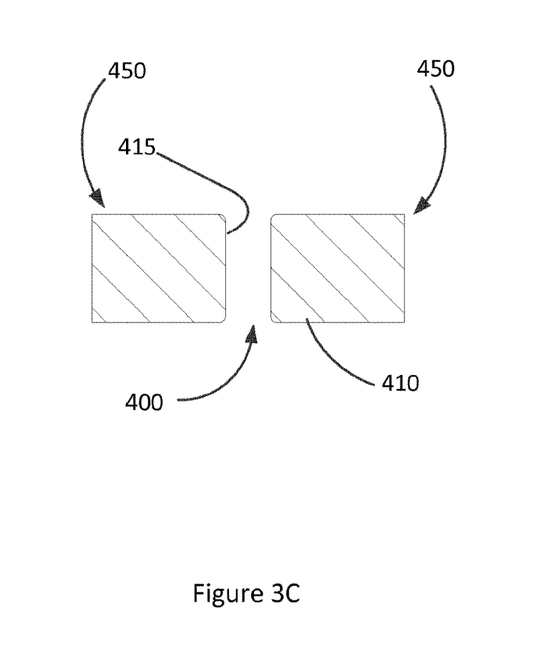
Figures 3D, 3E:
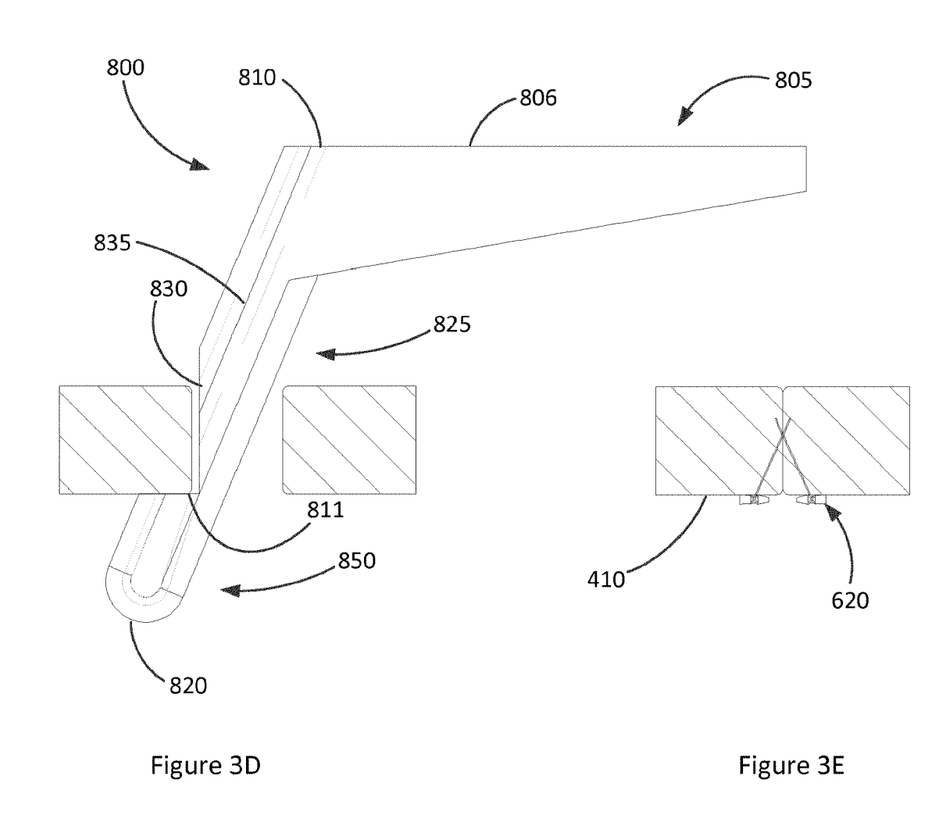

FIG. 1A shows an example of the device 50 with a driver tool 500 inserted through it. A driver tool or suture passer may be passed through the section of the device 300 that will be position adjacent to the tissue requiring suturing to ensure an appropriate recruitment of tissue. A deployment channel 320 is configured with an optimal angle suture stability post deployment. The device features a landing zone 110 that cooperates with the tissue being retracted and a lip 105 that ensures tissue stability. As shown in FIG. 2, a finger hole is 130 is provided for controlling the device in this configuration but a handle or other interface could also be provided. A slot could also be provided in the deployment channel 320 to ease suture removal after deployment.

Figure 1B:
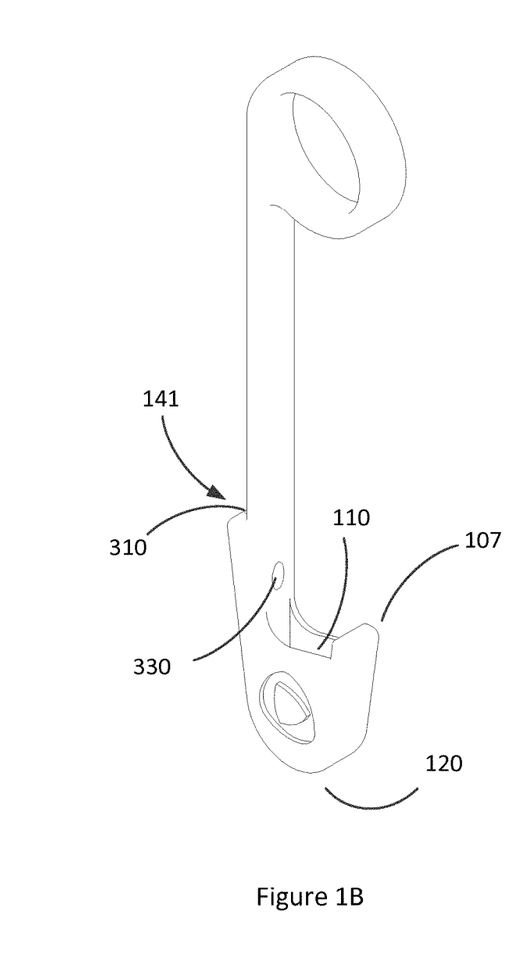

FIG. 1B show the device in a projected view and illustrates the position of the suture channel entrance 310 and exit 330. The device also features a sharps protector 115 which prevents the sharp tip of the suture passer or anchor driver from causing injury. This is an advantageous feature as it obviates the need for internal visualisation during deployment in laparoscopic procedures and provides additional safety in open surgery settings. The tip of the device 120 is configured to be atraumatic to facilitate safe and efficient delivery.

FIG. 2A shows a defect 400 with tissue 450 either side. In the provided configuration the device is inserted through the defect and the grip is position to provide good anchoring into the tissue. The driver 500 may be inserted at this point or the tool may be rotated to retract the edges of the defect towards the visual field of the user for easier deployment prior to driver deployment. In the configuration shown a suture anchor 600 comprised of a suture 610 and an anchor 620 is deployed through each side of the defect enabling subsequent approximation. The device can be repeatedly deployed in sets of two to enable longer defects to be approximated. In the scenario where a suture passer is used the suture would be deployed through one side and then picked up thorough the opposite side using the retractor guide to deliver the passer in each instance.

As described above, the present teaching provides a suture delivery device 50 that operably may be used to deliver suture and/or anchors within a defect. The device 50 comprises a head portion 130, a body portion 140 and a foot portion 150. The device is configured such that the foot portion 150 is operably presented first into a defect 400 and engages with an inner surface 410 of the defect. The body portion 140 comprises a suture driver guide channel 320 having an entry port 310 provided on a first side of the body portion 140 and an exit port 320 provided on a second side of the body portion 140. The foot portion 150 defines a landing zone 110 at or proximal to the exit port within which at least a portion of surface of the defect is operably received. In this way and as shown in FIG. 2, a suture driver passing through the suture driver guide channel 320 will exit the exit port and pass into the surface of the defect within the landing zone. The foot includes an anchoring feature 107 which anchors the device and facilitates tissue manipulation during use.

The foot portion comprises an inner surface 200 provided proximal to the landing zone and an outer surface 210 arranged distally to the landing zone. The inner surface provides an abutment surface defining a limit of travel of a suture driver passing through the suture driver guide channel. The foot portion further comprises a blunt leading surface 220. The foot portion further defines a volume 205 having an open mouth, the landing zone being accessed through the mouth. The volume 205 may be a closed volume as shown in FIG. 2 or may be provided as an open volume having gaps or apertures provided proximal to the leading surface 120. The foot portion may further comprises a lip 105, the lip defining an engagement surface for contacting with and gripping against the inner surface of the defect. In this way, on gripping against the inner surface of the defect, at least a portion of the defect is received into the mouth of the foot portion.

As shown in FIG. 1B, the exit port is located above the mouth and the guide channel is angularly orientated relative to the mouth of the foot portion such that operably, on receipt of at least a portion of the defect into the landing zone, a suture driver passing through the guide channel will pass through first and second surfaces of the defect prior to contact with the abutment surface.

The body 140 comprises a shoulder region 141, the entry port 310 being defined in the shoulder region. Advantageously, the width of the body portion below the shoulder 141 is greater than the width of the body portion above the shoulder. In this way the length of the channel 320 may be maximised to provide additional structural integrity to the path and also ensure that the angle of attach of the driver when presented through the channel is maintained. By locating the entry port 310 within the shoulder region it will also be appreciated that visualisation of presentation of the driver 500 is facilitated.

The guide channel in this arrangement is desirably orientated at an angle in the range 20 to 45 degrees relative to a vertical axis of the body. More typically, the present inventor has found that by providing the guide channel within the body so as to be orientated at an angle of about 30 degrees relative to a vertical axis of the body that it is easier to ensure accurate presentation of suture—with anchor as appropriate—to a particular portion of the defect as shown in FIG. 2.

The guide channel is typically positioned at a desirable distance (within the range 5 to 10 mm has been found optimum) relative to an edge of the device to enable repeatable spacing between sets of deployed sutures along the length of a defect.

As was described above the device is arranged such that the foot portion is operably presented first into a defect and engages with the defect. The device is arranged such that it will contact with both the side wall 415 of the defect and the inner surface 410 of the abdominal wall. By contacting the abdominal wall in two planes, and receiving tissue into a tissue receiving portion defined in the device between the two contacting surfaces, the present teaching advantageously ensures that the suture driver 500 when passing through the suture driver guide channel 320 will exit the exit port 330 and pass into the surface of the defect within the landing zone. The surface within which the exit port is defined is a second surface of the guide device and as shown in FIG. 2 operably abuts against the side wall of the defect. The foot portion defines a contact surface 105 that operably abuts against the inner surface of the abdominal wall such the second surface is substantially perpendicular to the foot portion contact surface.

While not shown in the Figures, the device may be configured such that the body comprises an access channel or slot along the length of the guide channel. The purpose of the slot is to facilitate extraction of suture that has been passed through the guide channel and is located within the defect without requiring a removal of the device from the defect. So as to restrict the escape from the guide channel of other deliverable elements, the slot has a diameter smaller than the diameter of the guide channel. Typically the diameter of the slot is about 0.5 to 1.5 mm.

As shown in the Figures, the device head portion 130 provides a contact surface to user engagement to facilitate a location of the device within the defect. In this exemplary arrangement, the head portion is offset from a longitudinal axis of the body. Similarly, and evident from the side view of FIG. 1A, the foot portion 150 is also offset from a longitudinal axis of the body. By having each of the head portion and foot portion offset to the same side of the body, and desirably wherein the head portion is orientated above the foot portion the user or operator of the device is assisted in identification of the location of the foot portion within the defect when the foot portion is not visible to an operator—such as when the foot portion is located through a defect and within the abdominal cavity—such as shown in FIG. 2.

In this arrangement of FIG. 2 it is clearly shown that each of the foot portion and the head portion extend laterally away from the body portion and are offset an equal distance from the longitudinal axis of the body portion.

The side surface of the body facilitates a retraction of the abdominal wall or other fascial layer so as to provide surgical access. The device therefore provides a dual function as a retractor and a suture delivery device. This device may be provided singularly or as part of a suture delivery kit comprising the device as described previously in combination with a suture driver arranged to deliver suture through the guide channel. With such a kit operable passage of the suture driver through the defect effects delivery of the suture though a first and second surface of the defect, as shown in FIG. 2. When the suture is coupled to an anchor, the kit may be used to deliver anchors through at least a portion of a defect. Rotation of the device after delivery of a first anchor at first side of the defect then allows the user to facilitate delivery to a second side of the defect—FIG. 2 shows an already delivered anchor on the right hand side while the device is now presented and arranged to deliver the anchor to the left hand side.

In the alternative arrangement of FIG. 3 a guide 800 comprises a handle portion 805 and a guide portion 825 and a foot portion 850. The guide portion 825 is operably inserted into a defect defined within the abdominal wall. The guide portion comprises a tissue receiving cut-out portion 870 which is defined within the body of the device. First 811 and second 815 surfaces extend inwardly from the outer surface of the guide to define the tissue receiving cut-out portion and are arranged such that in use, abdominal wall tissue will invaginate into the tissue receiving cut-out portion 870 and contact against the surfaces 811 and 815. A guide channel 835 is defined within body of the guide and leads to the tissue cut out portion. The guide channel 835 comprises a proximal opening 810 on a first, operably upper, surface 806 of the guide 800 and terminates from a distal opening 830. The distal opening 830 is defined within the second surface 815, which operably defines an upper, surface 815 of the tissue receiving cut-out portion 870. The trajectory of the channel is configured such a driver delivered through the channel will intersects with and pass through tissue that may be disposed within the cut-out portion.

A driver 500 and anchor 230 as previously described may be used to deliver an anchor through the tissue which is received within the tissue receiving cut-out portion. Upon exiting the distal opening 830 and travelling through the tissue, the orientation of the guide channel 835 serves to direct the driver into a receiving chamber 855 defined within the first surface 811 of the tissue receiving cut-out portion. This chamber 855 comprises inner surfaces which protect the inner organs from puncture in a similar fashion to that described above with reference to FIGS. 1 and 2.

In this embodiment the distal opening of the guide channel exits on a flat surface 815. An alternative arrangement would be that the surface below the exit was undercut. In this arrangement, an undercut is defined below the distal opening 830 such that the surface 815 does not extend in a planar continuous fashion to the intersection with the surface 811. This could be advantageous in exaggerating the amount of tissue captured by the suture. It will be appreciated that the length and diameter of the suture guide channel can be dimensioned to limit the depth to which the tip of the driver extends, which would prevent the driver tip impacting against surfaces of the receiving chamber 855. Alternately the receiving chamber could be filled with a silicone gel, which would prevent particulate liberated from the bottom surface of the receiving chamber from being drawn out of the receiving chamber.

Similarly to what was described with reference to FIGS. 1 and 2 the device of FIG. 3 is arranged such that the foot portion 850 is operably presented first into a defect and engages with an inner surface of the defect. The device is arranged such that it will contact with both the side wall 415 of the defect and the inner surface 410 of the abdominal wall 450, Refer to FIGS. 3C-3E. By contacting the abdominal wall in two planes, and receiving tissue into a tissue receiving portion defined in the device between the two contacting surfaces, the present teaching advantageously ensures that the suture driver 500 when passing through the suture driver guide channel 835 will exit the exit port 830 and pass into the surface of the defect within the landing zone. The surface within which the exit port is defined is a second surface of the guide device and as shown in FIG. 3C operably abuts against the side wall of the defect. The foot portion defines a contact surface 105 that operably abuts against the inner surface of the abdominal wall such the second surface is substantially perpendicular to the foot portion contact surface.

Figure 4:
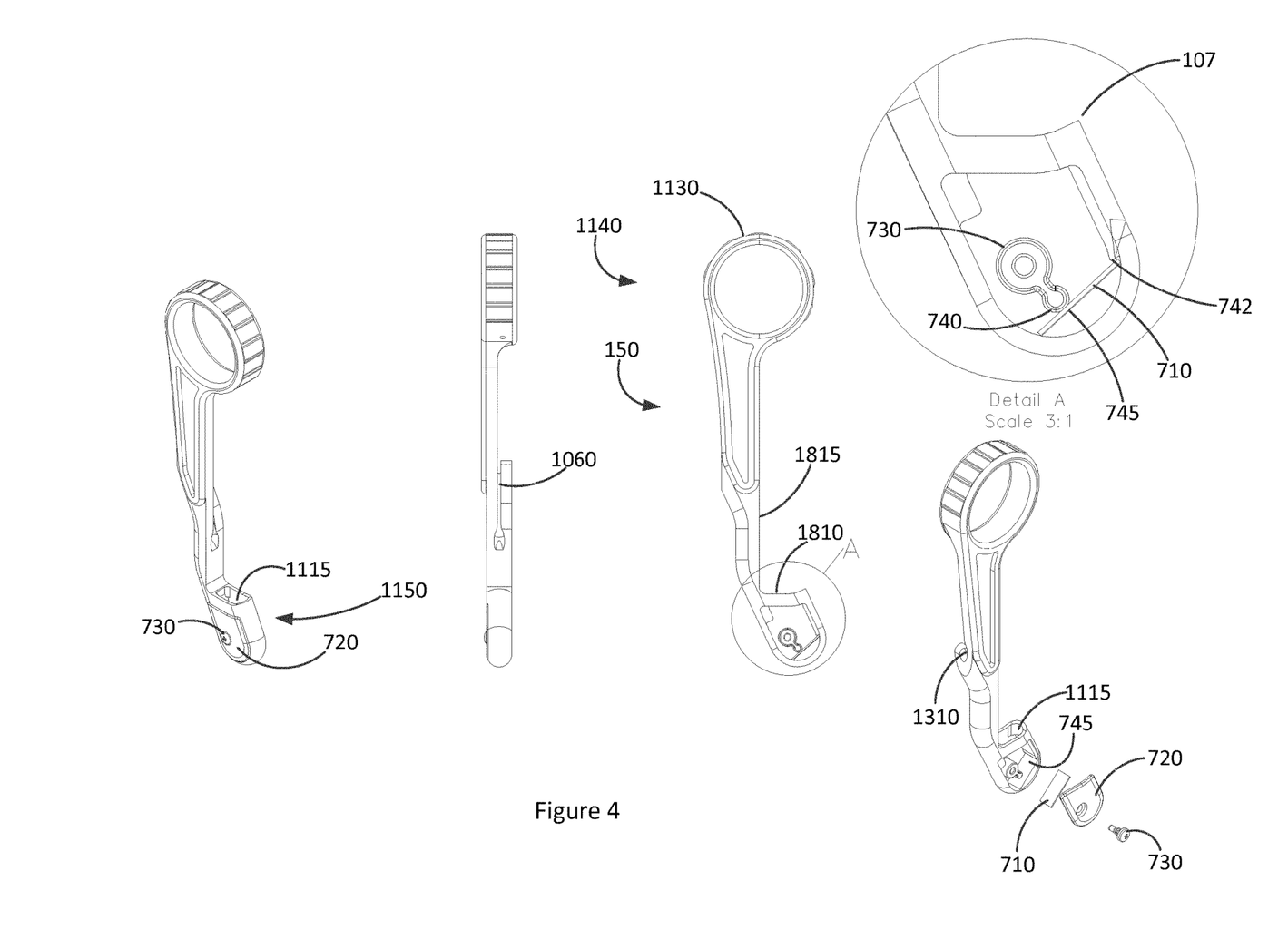
FIGS. 4 and 5 show multiple views of another embodiment of the device in accordance with the present teaching.

Turning now to FIG. 4, another exemplary suture delivery system in accordance with the present teaching is shown. In this arrangement the system comprises multiple components which are then assembled to form the final part, whereas the guides of FIGS. 1-3 are a single moulded piece. With this arrangement surfaces of the receiving portion are replaceable. Such an arrangement advantageously addresses potential issues arising from multiple contacts with the same surface. As will be appreciated from the above, the present teaching uses the inner surfaces of the receiving portion as a stop against which the driver contacts during use. A potential difficulty with having drivers repeatedly contact the same surface, which can arise for example in scenarios where multiple anchors are being deployed, is that the sharp needle tip of the driver may repeatedly contact the same portion of the guide and over time it may begin to dislodge some of the guide material. In this embodiment, the receiving portion is modified to incorporate a more resilient material—in this example a stainless steel shim 710—as a contact surface which is located at the base of the receiving chamber 1115. By providing a contact surface at the base of the receiving chamber, the driver needle portion is directed—by the orientation of the guide channel 1320 (Refer to FIG. 5) into preferential contact with the contact surface. The material that is used in fabricating the contact surface is less likely to be damaged by the needle end portion and thus reduces the possibility of the integrity of the guide being compromised with reduced possibility of dislodged material being introduced into the body cavity during use.

The contact surface may be retained within the receiving portion in any one of a number of different ways. FIG. 4 shows a particularly advantageous arrangement whereby the stainless steel shim is retained by a shoulder 745 on the inner wall of the guide and a pillar 740. In this embodiment the pillar 740 is shown as an elongation of a screw receiving pillar, but it will be acknowledged that these two adjoined pillars could be formed as a single piece, that is if the screw position was adjusted, or they could be two separate entities. To allow for assembly a cap 720 is provided, which can be screwed into position with the screw once assembly is completed. It will further be appreciated by those skilled in the art that the same effect could be achieved a number of ways. For example, the cap 720 could be designed with clip features, such that the screw is not necessary to retain the cap. In another embodiment the side wall of the receiving portion could feature j shaped channel into which a j-shaped shim is placed. Alternately, the u-shaped inner surface as per FIG. 2 could be modified at the top to add two bumps, which could be used to retain a u-shaped steel shim. Further, the shim could be biased, such that upon placement in the receiving portion, it exerts an outward force, which helps maintain its position.

Depending on the tolerances of the stainless steel shim 710 and its fit within the guide there may be an effective rattling of the component, which may be undesirable. Is such a scenario the bottom surface 745 of the receiving channel 1115 may be coated with a silicone fluid or the like, which will retain the stainless steel shim due to surface tension.

An advantage of the stainless steel shim in the guide, is that when the driver is passed through the guide and the sharp tip bottoms out on the stainless steel shim, an audible click is generated which will provide audible feedback in addition to the tactile feedback that is already generated by the contact of the two elements. The user is then provided with reassurance that the anchors have been successfully delivered through the abdominal wall.

Another feature of the guide of FIG. 4 is the incorporation of a suture release slot 1060. This slot allows the suture to be released from the guide. In using the guide of FIG. 1, once the first anchor is delivered, the trailing suture remains in the guide channel until the guide is removed completely over the trailing suture. The advantage of the suture release slot 1060 is that once the anchor is delivered, the suture can be pulled taut, and as the guide is pushed away from the tissue wall, the suture is released from the guide. The guide can then be rotated in situ for delivery of a second anchor on the opposing wall, without having to remove the guide from the defect.

An alternate embodiment would provide an additional slot 1900 in the foot portion of the guide. Such an arrangement is shown in FIG. 10E and illustrates how such a slot 1900 could be used to receive a suture 610. A larger diameter opening 1910 is provided at the base of the slot. This opening 1910 would allow the suture 610 to pass freely when pulled from either side. A narrowing in the slot is provided by raised shoulders 1905A and 1905B. Such a narrowing prevents the suture from being accidently released from the slot 1900 and allows the suture 610 to be easily loaded, by laying it across the slot and pulling it in a downward direction, in a manner similar to securing using a cleat. Such an arrangement could be advantageously used to deliver suture to an intra-abdominal space. The user could then use a conventional suture passer 2500 through the opening 1310 defining the entrance to the guide channel 1320 (previously referred to in FIG. 5) to pick up the suture that is located within the landing region. Such an arrangement is evident from inspection of FIG. 10A and advantageously provides a safe means of creating a closed loop closure as the receiving chamber 1115 of the guide protects from over insertion of the suture passer.

Figure 10A:
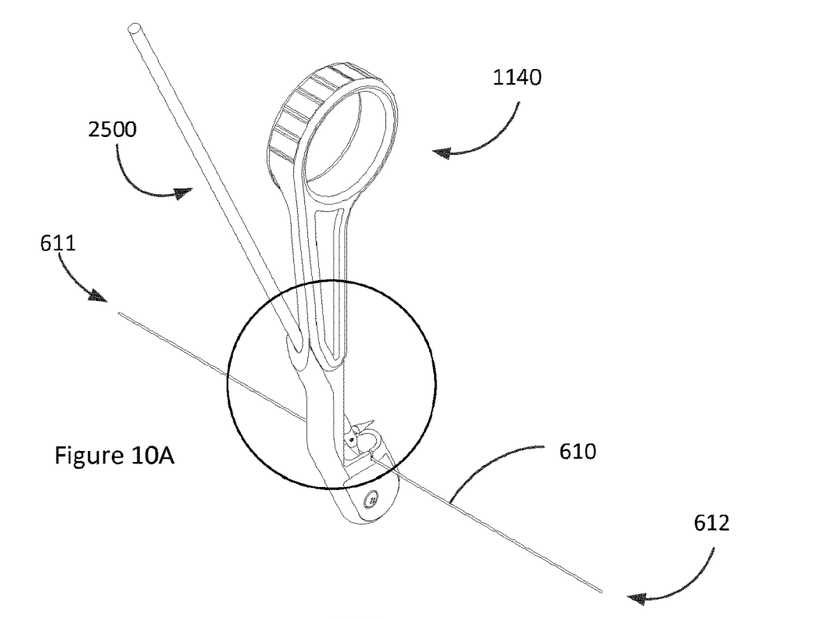
FIG. 10 shows multiple view of the device of FIGS. 4 and 5 configured to deliver a loop of suture.
Figure 10B:
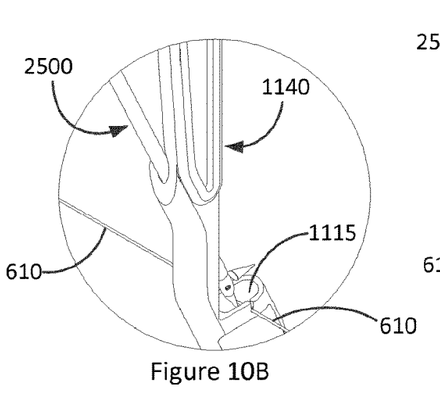
Figure 10C:
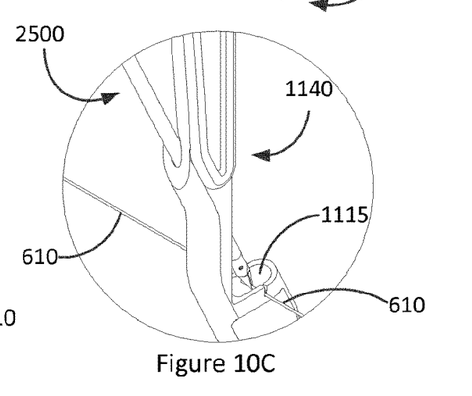
Figures 10D, 10E:
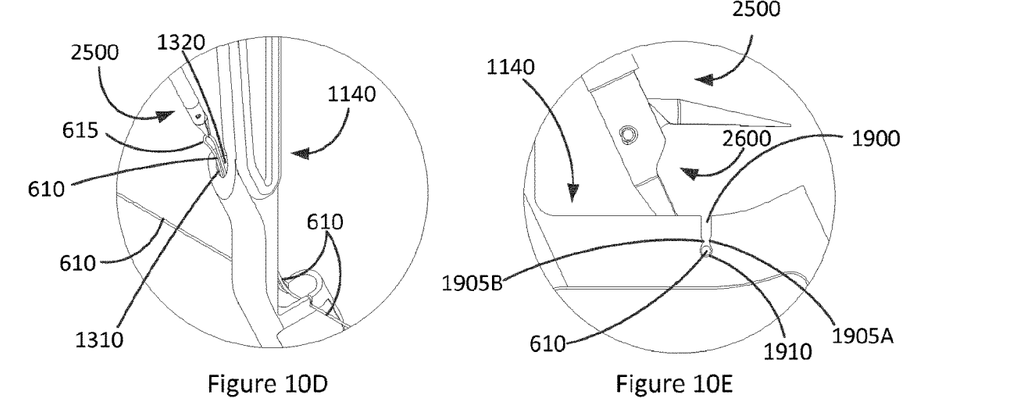

To use the device of FIG. 10A with reference to FIG. 10B-FIG. 10D:
 a. The user loads suture 610 onto the guide 1140,
 b. The guide 1140 is then passed through a defect in the abdominal wall
 c. The suture grasper 2500 is passed through the guide and is manipulated to grasp the suture 610.
 d. Once the suture is held in the jaws 2600 of the grasper, it is retracted until the suture exits the opening 1310
 e. As the suture loop 615, is drawn further outside the body, the suture would pull completely through the opening
 f. The guide could then be removed, from the defect and be reloaded with the suture.
 g. The guide can them be repositioned in the defect on the opposite side, and step a-f be repeated.
 h. The guide is removed from the defect leaving a loop of suture in the defect, which can be tied with an appropriate surgical knot.

One end of the suture, 611 for example could be presented with a stopper knot, which would prevent the suture pulling through the opening 1910 on the guide, which would ensure that the suture pulls free from one side only. An alternative arrangement would be to provide the opening 1910 without suture. This arrangement would be more secure in terms of preventing the suture from pulling out through the slot, but would be more time consuming in terms of loading.

Figure 5:
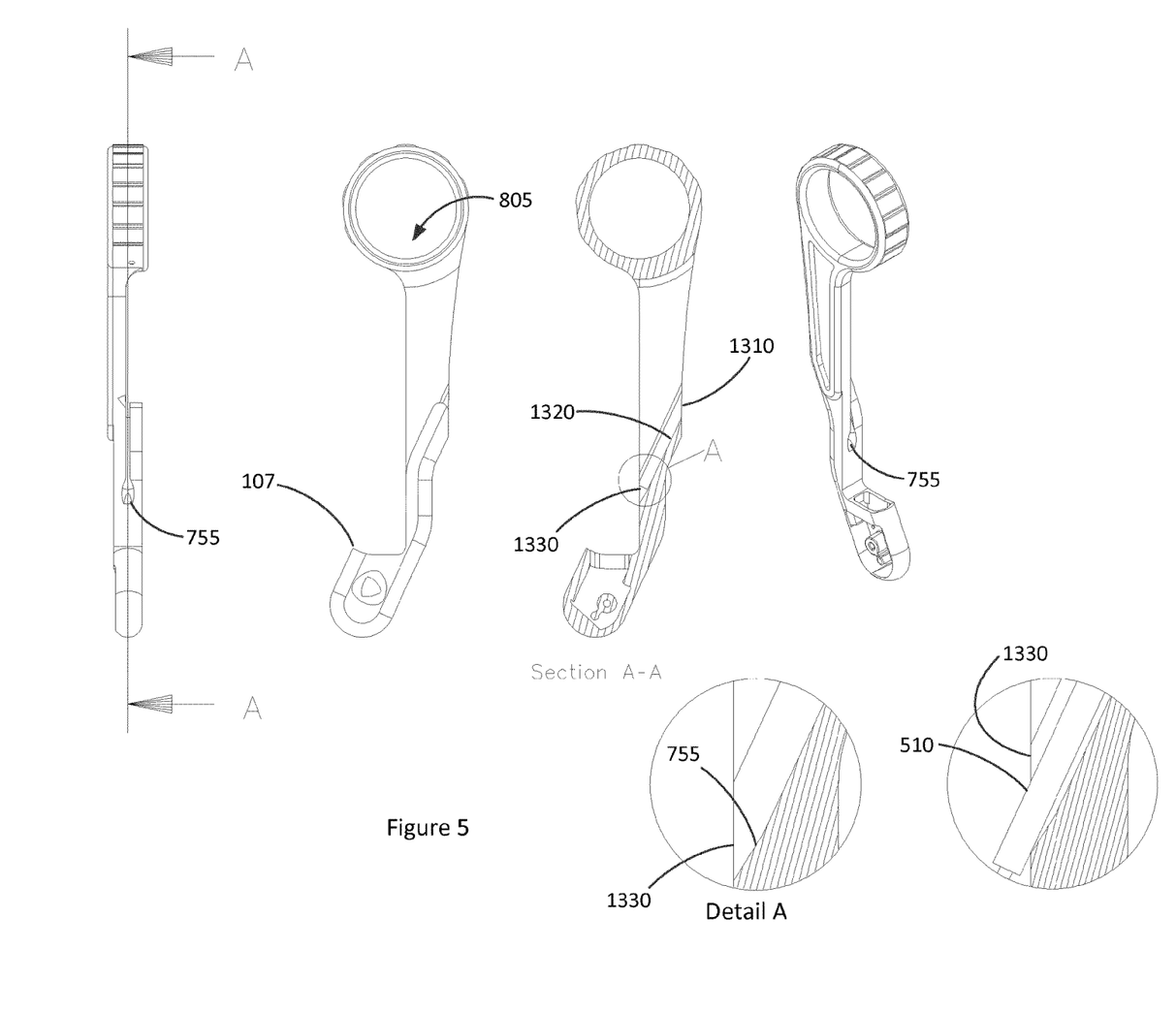
Figure 6:
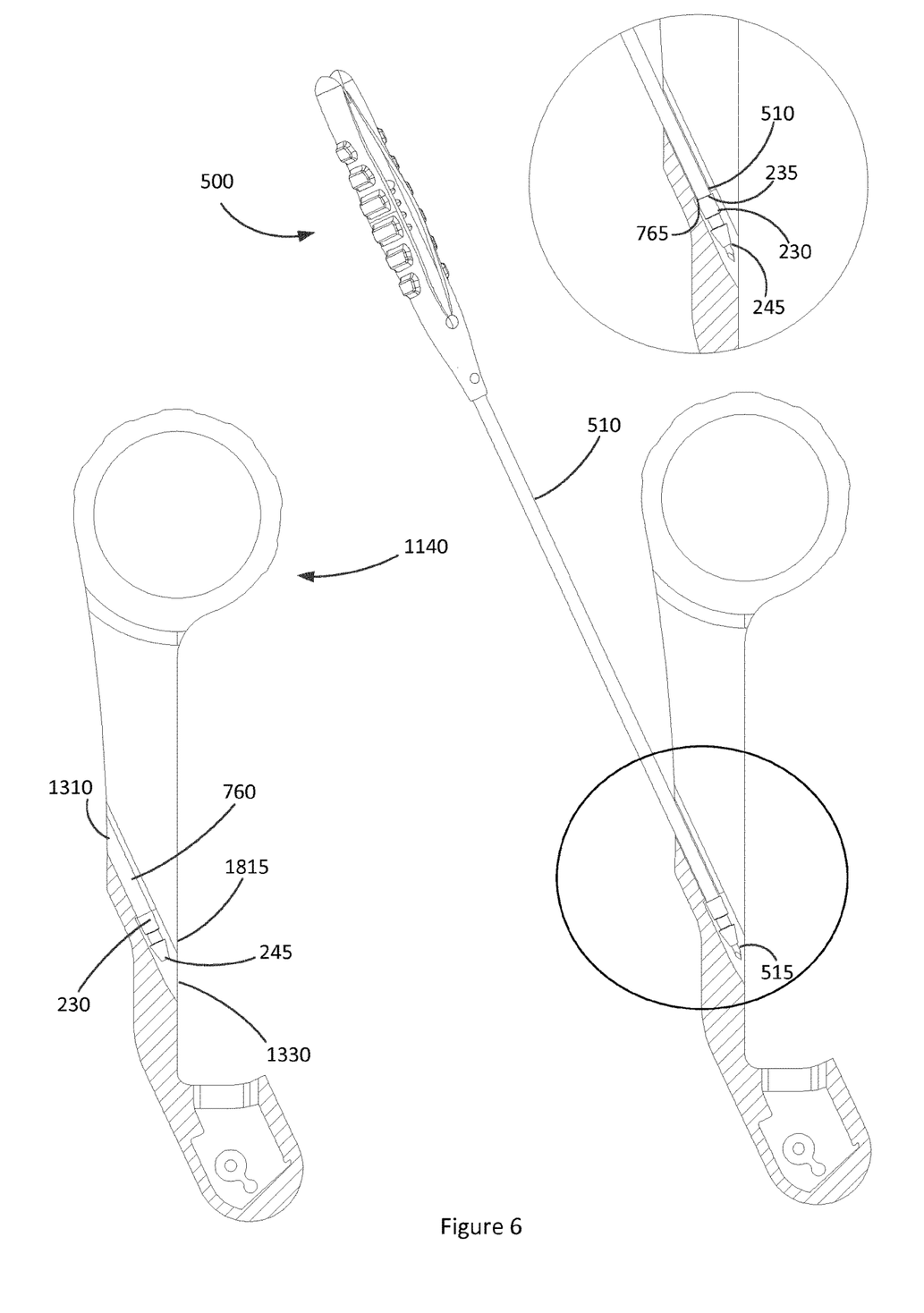
FIG. 6 shows a section views of the device of FIGS. 4 and 5 with a preloaded anchor.

FIG. 5 illustrates another feature of the guide of FIG. 4 whereby the needle guide channel 835 features an internal ramp 755. The benefit of such a feature is that it effects a reduction in the clearance within the channel, when the driver is delivered through, which has the effect of giving a more consistent bite through the tissue. This is an effect caused by the reduced diameter of the driver shaft 510, as is seen in FIG. 5. An alternative arrangement is shown in FIG. 6 where the guide channel features a reduced diameter portion 760 proximal to the proximal opening of the needle guide channel. In using this guide, the anchors would be loaded, firstly into the guide by pushing the proximal end of the anchor 235 into the guide exit 1330, i.e. in a direction opposite to that in which they will ultimately be delivered into the tissue, and then using the suture (not shown) to pull the anchor into the step 765. The driver is then presented through the opening 1310 of the guide and as it passes through, the anchor is picked up by the stepdown portion of the driver.

Figure 7A:
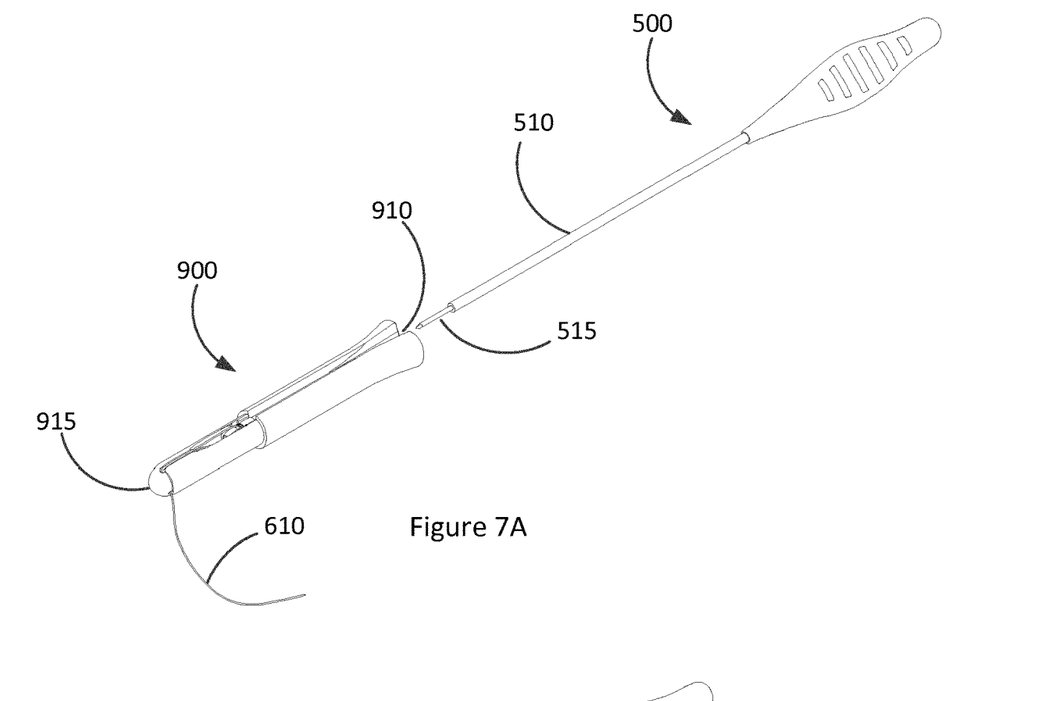
FIGS. 7 and 8 show alternative arrangement for the reloading or delivery of anchors through a guide channel in accordance with the present teaching.
Figure 7B:
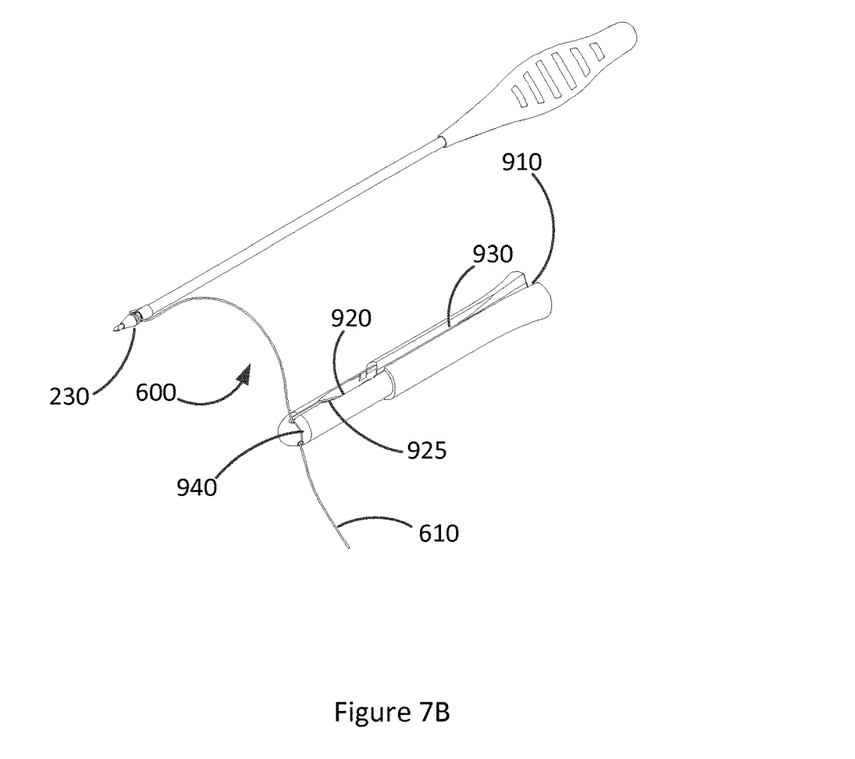
Figure 8A:
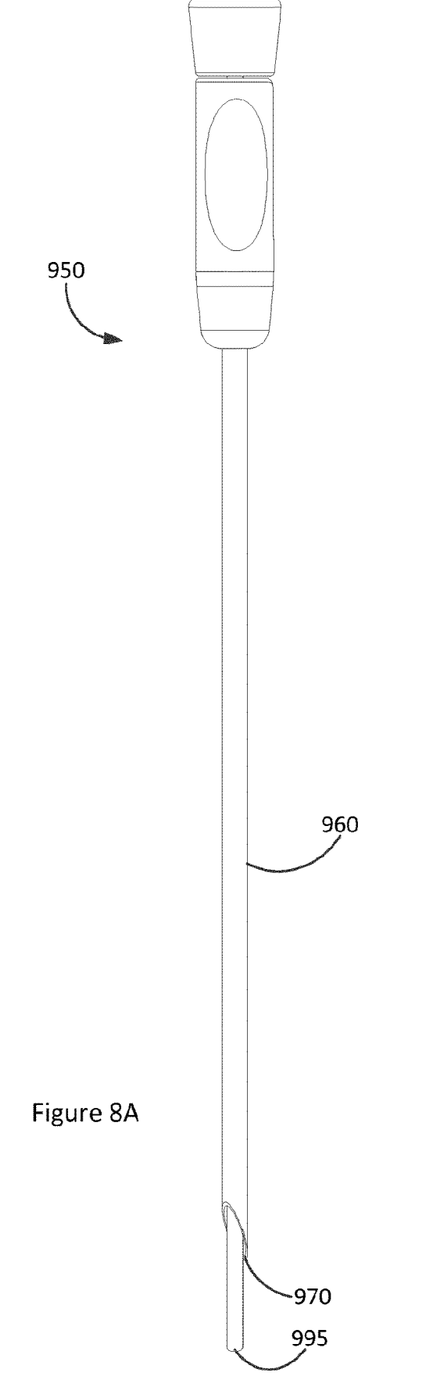
Figure 8B:
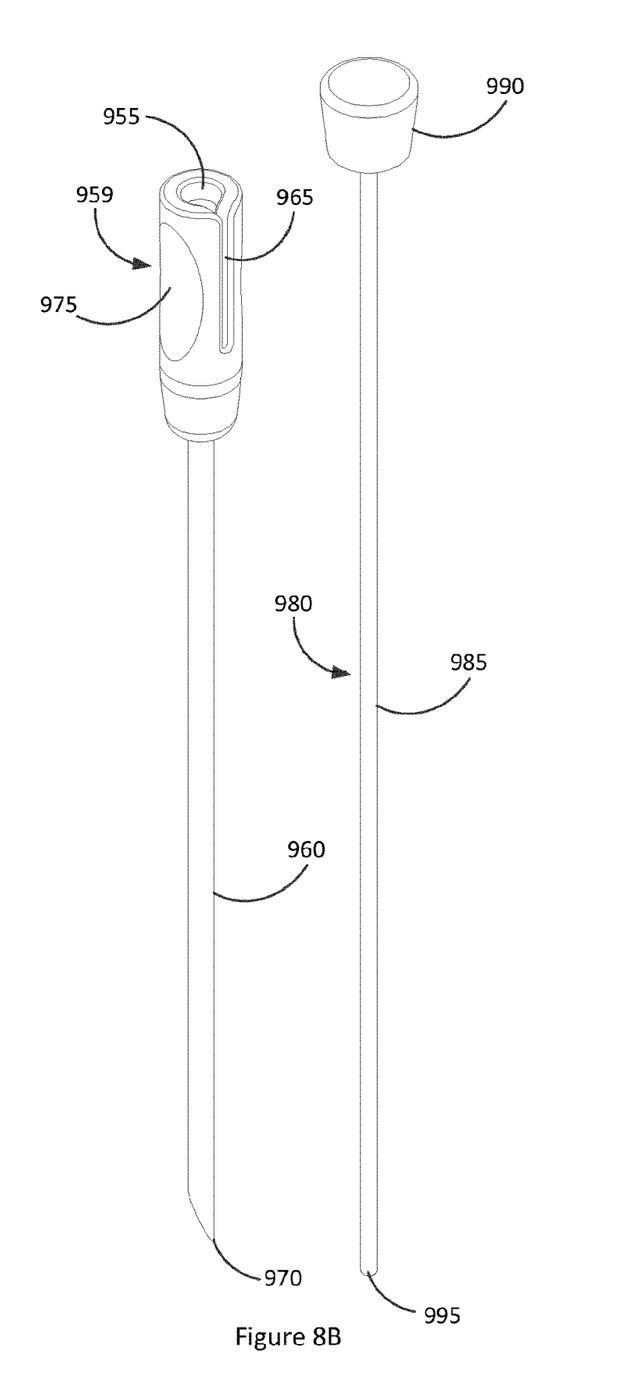

Further examples of reloading anchors onto drivers are shown in FIGS. 7 and 8, which may be used in combination with the guides of FIGS. 1-5. There is shown herein a reloader tool 900 which comprises a proximal opening 910, an anchor receiving portion 920 and a suture cleat 940. The anchor is loaded into the anchor receiving portion, and the trailing suture is secured in the cleat 940. The driver 500 is passed through the proximal opening. The internal geometry (not shown) serves to align the driver such that the stepdown portion 515 will be centred on the anchor and pick it up, as it is advanced through the reloader tool 900. The distal end of the anchor receiving portion 920 features a ramp 925. As the driver advances this ramp provides resistance against forward motion of the anchor, allowing it to be picked up by the driver, and secondly as the driver is advanced the misalignment of the ramp forces the driver into the exit slot 930. The suture cleat is designed such that the inside of the cleat is a circular profile and that as the anchor is advanced, the suture trails from the cleat.

The device 950 of FIG. 8 comprises an obturator 980 and a guide 950. The obturator 980, which could be spring-loaded to facilitate a Veress needle type protected delivery—comprisesa proximal handle 990 and a shaft 985 which are joined. The handle 990 allows the user to handle the obturator and remove it from the guide portion. The guide 950 comprises a proximal portion 959 joined to a shaft 960.

The shaft 960 terminates distally in a sharp tip 970. When the obturator 980 is in place it serves to protect the sharp tip. The proximal portion 959 has a lead-in 955 to a lumen disposed through the proximal portion 959, which further extends completely through the device via the shaft, through which an anchor 230, such as that shown in previous embodiments may be introduced. The anchor can be pulled further into the lumen until the suture is as distal as it can be in the slot 965. Finger grips 975 are provided on the external surface of the proximal portion 959. These are illustrated as smooth, but could be textured to improve grip. The device could then be passed through an abdominal wall, or through a prosthetic material, such that the distal end is inside the abdominal space, interior to the inner abdominal wall or prosthetic material. The anchor can then be delivered by passing the obturator back though the guide. The anchor is pushed distally through the guide, until it exits in the intra abdominal space. The guide and obturator can then be retracted leaving the anchor in situ. The remaining anchor can then be used in conjunction with other such anchors to approximate tissue or prosthetic material.

Figure 9:
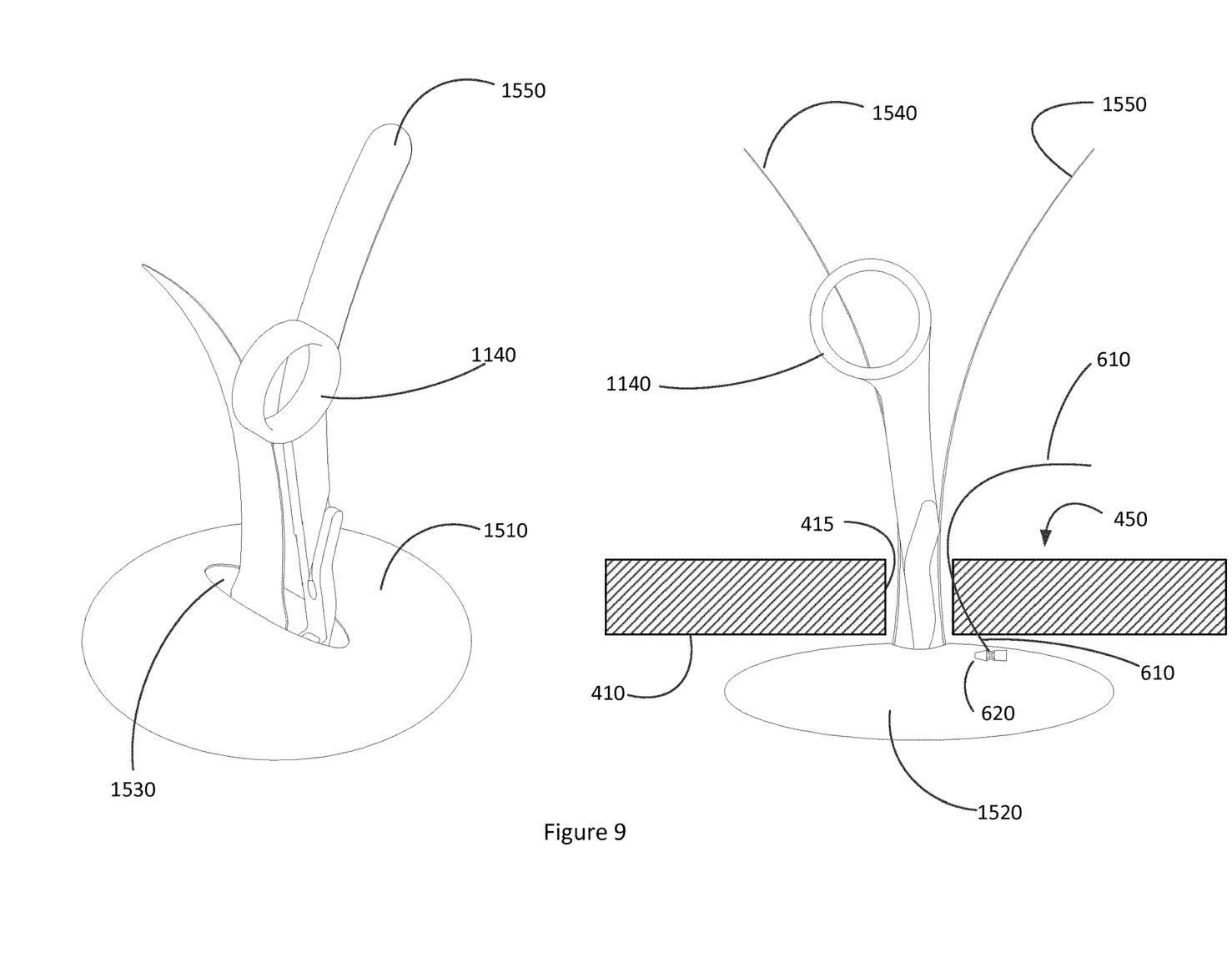
FIG. 9 shows the device of 4 and 5 used to secure a prosthetic mesh.

Another example of use of a guide 1140 in accordance with the present teaching is illustrated in FIG. 9. The guide 1140 interacts with a prosthetic device 1500. The prosthetic device 1500 features an opening 1530 on the abdominal wall engaging side 1510. The opening has a pair of straps 1540 and 1550 attached to the device 1500 and which can be used to manipulate the prosthetic device 1500. The prosthetic device further comprises an organ contacting side 1520, which in combination with 1510 defines an internal space in the device, which is accessed through the opening 1530. In use the distal portion of the guide 1150 is inserted into the prosthetic device through the opening 1530 guide. Anchors can then be delivered through the guide 1140, entering through the prosthetic material on the abdominal engaging potion 1510. The delivered anchor(s) are then retained in the inner volume of the prosthetic device. This enables fixation of the prosthetic device in situ, whilst also allowing and facilitating closure of the defect. Whilst shown as having a solid geometrical form, it will be appreciated that the form of the prosthetic may vary and could equally be provided in a mesh form.

While all of the embodiments above illustrate a single delivery channel, it will be appreciated by those skill in the art, that a similar guide could be provided featuring multiple delivery channels, to allow for anatomical differences, for example abdominal wall thickness in obese and non-obese patients, wherein the angle of the guide channel is varied to achieve the desired outcome.

As detailed above, in accordance with aspects of the present teaching, the suture/anchor assembly may consist of a length of bioabsorbable suture attached to bioabsorable anchor, provided for example in the form of a length of bioabsorbable tubing or moulded geometry, and in one embodiment configured such that the assembly is t-shaped. The suture may be a braided or monofilament suture made from any application specific bioabsorbable or non-absorbable polymers. For fascial layer closure a USP size 0 suture is preferred. This material is ideally suited to an application where the suture maintains approximately 50% of its strength after two weeks. However it will be appreciated that the suture material may be changed depending on strength or mass loss requirements of the specific application.

While preferred arrangements have been described in an effort to assist in an understanding of the teaching of the present invention it will be appreciated that it is not intended to limit the present teaching to that described and modifications can be made without departing from the scope of the invention.

It will be appreciated that the exemplary arrangements or examples of devices have been described with reference to the Figures attached hereto. Where a feature or element is described with reference to one Figure, it will be understood that the feature or element could be used with or interchanged for features or elements described with reference to another Figure or example. The person of skill in the art, when reviewing the present teaching, will understand that it is not intended to limit the present teaching to the specifics of the illustrated exemplary arrangements as modifications can be made without departing from the scope of the present teaching.

The words comprises/comprising when used in this specification are to specify the presence of stated features, integers, steps or components but does not preclude the presence or addition of one or more other features, integers, steps, components or groups thereof.

The invention claimed is:

1. A laparoscopic surgical method comprising:
   a. inserting a suture delivery device through a defect in a tissue and positioning the suture delivery device on a first side of the defect, the suture delivery device comprising:
   a head portion, a body portion and a foot portion, the suture delivery device being configured such that the foot portion is operably presented first into the defect and engages with an inner surface of the defect, the body portion comprising a suture driver guide channel having an entry port defined in a first surface of the body portion and an exit port defined in a second surface of the body portion, wherein the foot portion defines a landing zone at the exit port within which at least a portion of a surface of the defect is operably received such that a suture driver passing through the suture driver guide channel will exit the exit port and pass through the surface of the defect within the landing zone, and the foot portion defines a volume having an open mouth, the landing zone being accessed through the open mouth, and wherein the second surface operably abuts against a side wall of the defect and the foot portion comprises a contact surface that operably abuts against an inner surface of an abdominal wall, the second surface is substantially perpendicular to the foot portion contact surface during insertion, and wherein the body portion comprises a suture release slot extending along a length of the suture driver guide channel, the suture release slot having a diameter smaller than the diameter of the suture driver guide channel;
   b. deploying one of a plurality of sutures through the tissue via the suture driver guide channel;
   c. moving the suture delivery device in situ to position the suture delivery device at a second or more location of the defect; and
   d. tying the one of the plurality of sutures to secure the defect.

2. The method of claim 1, wherein the foot portion contact surface and the second surface of the body portion are orientated substantially 80 to 110 degrees relative to one another.

3. The method of claim 2, wherein the foot portion contact surface provides an abutment surface defining a limit of travel of the suture driver passing through the suture driver guide channel.

4. The method of claim 1, wherein the volume is a closed volume.

5. The method of claim 4, configured such that on gripping against the inner surface of the defect, at least a portion of the defect is received into the open mouth of the foot portion.

6. The method of claim 1, wherein the foot portion comprises a lip, the lip defining an engagement surface for contacting with and gripping against the inner surface of the defect.

7. The method of claim 1, wherein the suture driver guide channel is angularly orientated relative to the open mouth of the foot portion such that operably, on receipt of at least a portion of the defect into the landing zone, the suture driver passing through the suture driver guide channel will pass through first and second surfaces of the defect prior to contact with the foot portion contact surface.

8. The method of claim 1, wherein the diameter of the suture release slot is about 0.5 to 1.5 mm.

9. The method of claim 1, wherein the suture delivery device comprises a plurality of suture driver guide channels.

10. The method of claim 1, wherein the body portion defines an undercut below the exit port.

11. The method of claim 1, wherein the suture driver guide channel comprises a ramp.

12. The method of claim 1, wherein the landing zone comprises the contact surface against which the suture driver operably contacts.

13. The method of claim 12, wherein the contact surface of the landing zone providing a stop limiting further introduction of the suture driver through the suture delivery device.

14. The method of claim 12, wherein the contact surface of the landing zone comprises a stainless steel shim which operably provides auditory and tactile feedback.

15. The method of claim 1, wherein the suture delivery device is configured for delivery of anchors, the suture delivery device comprising at least one anchor preloaded in the suture driver guide channel.

16. The method of claim 1, wherein the foot portion comprises a suture retention feature to retain a suture of the plurality of sutures during a delivery of the suture delivery device into the defect, the suture delivery device being configured to operably engage with a suture grasper which on receipt through the suture driver guide channel effects release of a retained suture from the suture retention feature.

17. The method of claim 1, wherein the foot portion comprises an anchoring feature.

18. The method of claim 1, further comprising:
repeating b and c along a length of the defect.

19. The method of claim 1, wherein moving the suture delivery device includes rotating the suture delivery device.

20. The method of claim 1, wherein the suture delivery device is configured such that the foot portion with the open mouth is operably presented first into the defect.

* * * * *